US012651163B2

(12) United States Patent
Mudassir et al.

(10) Patent No.: US 12,651,163 B2
(45) Date of Patent: Jun. 9, 2026

(54) METHOD AND SYSTEM TO DETERMINE AN OPTIMAL SET OF ATOM CENTERED SYMMETRY FUNCTIONS (ACSFs)

(71) Applicant: Tata Consultancy Services Limited, Mumbai (IN)

(72) Inventors: Mohammed Wasay Mudassir, Hyderabad (IN); Sriram Goverapet Srinivasan, Chennai (IN); Mahesh Mynam, Hyderabad (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 571 days.

(21) Appl. No.: 18/206,205

(22) Filed: Jun. 6, 2023

(65) Prior Publication Data

US 2024/0028889 A1 Jan. 25, 2024

(30) Foreign Application Priority Data

Jun. 9, 2022 (IN) .............................. 202221033122

(51) Int. Cl.
*G06N 3/08* (2023.01)
*G06N 5/02* (2023.01)
*G16C 10/00* (2019.01)

(52) U.S. Cl.
CPC ................. *G06N 3/08* (2013.01); *G06N 5/02* (2013.01); *G16C 10/00* (2019.02)

(58) Field of Classification Search
None
See application file for complete search history.

(56) References Cited

U.S. PATENT DOCUMENTS

2018/0285731 A1* 10/2018 Heifets .................... G06N 3/08

FOREIGN PATENT DOCUMENTS

| | | | |
|---|---|---|---|
| DE | 2019 217 222 A1 | 5/2020 | |
| EP | 3 433 780 B1 | 6/2021 | |
| WO | WO-2021243106 A1 * | 12/2021 | ............. G06N 3/044 |

OTHER PUBLICATIONS

Eckhoff et al., "High-dimensional neural network potentials for magnetic systems using spin-dependent atom-centered symmetry functions," npj Computational Materials, 7:170 (2021) (Year: 2021).*

(Continued)

*Primary Examiner* — Andrew J Steinle

(74) *Attorney, Agent, or Firm* — FINNEGAN, HENDERSON, FARABOW, GARRETT & DUNNER LLP

(57) ABSTRACT

This disclosure relates generally to method to determine an optimal set of atom centered symmetry functions. One or more parameters associated with one or more atom centered symmetry functions (ACSFs) are received. An initial set of ACSFs is generated by varying the one or more parameters. A histogram with a prespecified bin size is constructed to obtain a distribution of value of each of the initial set of ACSFs. A pruned list of ACSFs is obtained based on width and maximum value of the distribution of the value of initial set of ACSFs. The pruned list of ACSFs is sorted in decreasing order of spread to obtain a sorted list of ACSFs. An optimal set of one or more shortlisted ACSFs is determined by traversing through the sorted list of ACSFs. A high dimensional neural network potential is trained based on the optimal set of one or more shortlisted ACSFs.

15 Claims, 9 Drawing Sheets

(56)                    References Cited

OTHER PUBLICATIONS

Gastegger et al., "Machine learning molecular dynamics for the simulation of infrared spectra," Chem. Sci., 8 (2017) (Year: 2017).*

Eckhoff et al., "High-dimensional neural network potentials for magnetic systems using spin-dependent atom-centered symmetry functions," npj Computational Materials, 7:170 (2021).

Gastegger et al., "Machine learning molecular dynamics for the simulation of infrared spectra," Chem. Sci., 8 (2017).

Gastegger et al., "WACSF—Weighted Atom-Centered Symmetry Functions as Descriptors in Machine Learning Potentials," (2017).

Huang et al., "Material discovery by combining stochastic surface walking global optimization with a neural network," Chem. Sci., 8 (2017).

Li et al., "A critical comparison of neural network potentials for molecular reaction dynamics with exact permutation symmetry," Phys. Chem. Chem. Phys., 21 (2019).

Mueller et al., "Machine learning for interatomic potential models," J. Chem. Phys., 152 (2020).

Schütt et al., "SchNetPack: A Deep Learning Toolbox for Atomistic Systems," (2018).

* cited by examiner

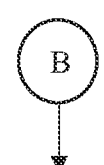

sorting, via the one or more hardware processor(s), the pruned list of ACSFs in a decreasing order of a spread to obtain a sorted list of atom centered symmetry functions (ACSFs) 312 determining, via the one or more hardware processor(s), an optimal set of a plurality of shortlisted ACSFs by traversing through the sorted list of ACSFs 314 reiteratively performing, via the one or more hardware processor(s), the step of traversing through the sorted list of ACSFs until there are no ACSF whose distance is greater than the predefined threshold with the prior shortlisted ACSFs 316 training, via the one or more hardware processor(s), a high dimensional neural network potential (HDNNP) based on the optimal set of the plurality of shortlisted ACSFs 318

FIG. 3D

METHOD AND SYSTEM TO DETERMINE AN OPTIMAL SET OF ATOM CENTERED SYMMETRY FUNCTIONS (ACSFs)

PRIORITY CLAIM

This U.S. patent application claims priority under 35 U.S.C. § 119 to: India Application No. 202221033122, filed on Jun. 9, 2022. The entire contents of the aforementioned application are incorporated herein by reference.

TECHNICAL FIELD

This disclosure relates generally to the field of modelling a chemical system, and, more particularly, to a method and system to determine an optimal set of atom centered symmetry functions (ACSFs).

BACKGROUND

High Dimensional Neural Network Potentials (HDNNPs) are an emerging class of classical force-fields that enable large length and time scale Molecular Dynamic (MD) simulations of chemical systems while retaining the accuracy of ab initio simulations. The chemical system is defined as a collection of interacting molecules. The NNPs are trained to learn a Potential Energy Surface (PES) of the chemical system by using the data obtained from high fidelity simulations such as ab initio MD. The main challenge in developing efficient and accurate HDNNPs for any chemical system is to identify optimal Atom Centered Symmetry Functions (ACSFs). The ACSFs transform the cartesian coordinates of atoms to ensure rotational, translational and permutational invariance of atom indices, which is otherwise violated when only cartesian coordinates are considered as inputs to the HDNNP. While the HDNNPs have been developed for a few systems, there is no systematic methodology or protocol to identify the right set of ACSFs. As a result, development of accurate and transferrable HDNNPs largely relies on only a trial-and-error approach based on certain heuristics currently.

SUMMARY

Embodiments of the present disclosure present technological improvements as solutions to one or more of the above-mentioned technical problems recognized by the inventors in conventional systems. For example, in one embodiment, a processor implemented method of determining an optimal set of atom centered symmetry functions (ACSFs) for developing neural network potentials is provided. The processor implemented method includes at least one of: receiving, via one or more hardware processor(s), one or more parameters associated with one or more atom centered symmetry functions (ACSFs); generating, via the one or more hardware processor(s), an initial set of atom centered symmetry functions (ACSFs) by varying the one or more parameters associated with the one or more ACSFs; computing, via the one or more hardware processor(s), a value of each of the initial set of ACSFs for each local environment in a training dataset; constructing, via the one or more hardware processor(s), a histogram with a prespecified bin size to obtain a distribution of the value of each of the initial set of ACSFs; pruning, via one or more hardware processor(s), the initial set of ACSFs to obtain a pruned list of ACSFs based on a width and a maximum value of the distribution of the value of each of the initial set of ACSFs;

sorting, via the one or more hardware processor(s), the pruned list of ACSFs in a decreasing order of a spread to obtain a sorted list of atom centered symmetry functions (ACSFs); and determining, via the one or more hardware processor(s), an optimal set of one or more shortlisted ACSFs by traversing through the sorted list of ACSFs. Each local environment corresponds to a region within a cut-off radius $(R_c)$ from a central atom. A pair-wise distance between a distribution of each of the one or more shortlisted ACSFs is greater than a predefined threshold.

In an embodiment, the training dataset include (a) one or more atomic configurations of a chemical system with data for each configuration including cartesian coordinates of one or more atoms, (b) forces acting on the one or more atoms, and (c) a potential energy for each of the one or more atomic configurations. In an embodiment, the one or more shortlisted ACSFs corresponds to (a) a first shortlisted ACSF, (b) a second shortlisted ACSF, (c) a third shortlisted ACSF, and subsequent shortlisted ACSFs. In an embodiment, an ACSF from the sorted list of ACSFs with a highest spread is identified as the first shortlisted ACSF. In an embodiment, the second shortlisted ACSF is identified by traversing through the sorted list of ACSFs until an ACSF is identified whose pair-wise distance with the first shortlisted ACSF is greater than a predefined threshold. In an embodiment, the third shortlisted ACSF and the subsequent shortlisted ACSFs are identified as functions whose pair-wise distance with both the prior shortlisted ACSFs is greater than the predefined threshold. In an embodiment, the step of traversing through the sorted list of ACSFs is reiteratively performed until there are no ACSFs whose pair-wise distance is greater than the predefined threshold with the prior shortlisted ACSFs. In an embodiment, a high dimensional neural network potential (HDNNP) is trained based on the optimal set of the one or more shortlisted ACSFs.

In another aspect, there is provided a system to determine optimal atom centered symmetry functions (ACSFs) for developing neural network potentials. The system includes a memory storing instructions; one or more communication interfaces; and one or more hardware processor(s) coupled to the memory via the one or more communication interfaces, wherein the one or more hardware processor(s) are configured by the instructions to: receive, one or more parameters associated with one or more atom centered symmetry functions (ACSFs); generate, an initial set of ACSFs by varying the one or more parameters associated with the one or more ACSFs; compute, a value of each of the initial set of ACSFs for each local environment in a training dataset; construct, a histogram with a prespecified bin size to obtain a distribution of the value of each of the initial set of ACSFs; prune, the initial set of ACSFs to obtain a pruned list of ACSFs based on a width and a maximum value of the distribution of the value of each of the initial set of ACSFs; sort, the pruned list of ACSFs in a decreasing order of a spread to obtain a sorted list of atom centered symmetry functions (ACSFs); and determine, an optimal set of one or more shortlisted ACSFs by traversing through the sorted list of ACSFs. Each local environment corresponds to a region within a cut-off radius $(R_c)$ from a central atom. A pair-wise distance between a distribution of each of the one or more shortlisted ACSFs is greater than a predefined threshold.

In an embodiment, the training dataset include (a) one or more atomic configurations of a chemical system with data for each configuration including cartesian coordinates of one or more atoms, (b) forces acting on the one or more atoms, and (c) a potential energy for each of the one or more atomic configurations. In an embodiment, the one or more shortlisted ACSFs corresponds to (a) a first shortlisted ACSF, (b) a second shortlisted ACSF, (c) a third shortlisted ACSF, and subsequent shortlisted ACSFs. In an embodiment, an ACSF from the sorted list of ACSFs with a highest spread is identified as the first shortlisted ACSF. In an embodiment, the second shortlisted ACSF is identified by traversing through the sorted list of ACSFs until an ACSF is identified whose pair-wise distance with the first shortlisted ACSF is greater than a predefined threshold. In an embodiment, the third shortlisted ACSF and the subsequent shortlisted ACSFs are identified as functions whose pair-wise distance with both the prior shortlisted ACSF is greater than the predefined threshold. In an embodiment, the one or more hardware processor(s) are further configured by the instructions to reiteratively perform the step of traversing through the sorted list of ACSFs until there are no ACSFs whose pair-wise distance is greater than the predefined threshold with the prior shortlisted ACSFs. In an embodiment, the one or more hardware processor(s) are further configured by the instructions to train a high dimensional neural network potential (HDNNP) based on the optimal set of the one or more shortlisted ACSFs.

In yet another aspect, there are provided one or more non-transitory machine readable information storage mediums comprising one or more instructions which when executed by one or more hardware processor(s) causes at least one of: receiving, one or more parameters associated with one or more atom centered symmetry functions (ACSFs), generating, an initial set of atom centered symmetry functions (ACSFs) by varying the one or more parameters associated with the one or more ACSFs; computing, a value of each of the initial set of ACSFs for each local environment in a training dataset; constructing, a histogram with a prespecified bin size to obtain a distribution of the value of each of the initial set of ACSFs; pruning, the initial set of ACSFs to obtain a pruned list of ACSFs based on a width and a maximum value of the distribution of the value of each of the initial set of ACSFs; sorting, the pruned list of ACSFs in a decreasing order of a spread to obtain a sorted list of atom centered symmetry functions (ACSFs); and determining, an optimal set of one or more shortlisted ACSFs by traversing through the sorted list of ACSFs. Each local environment corresponds to a region within a cut-off radius ($R_c$) from a central atom. A pair-wise distance between a distribution of each of the one or more shortlisted ACSFs is greater than a predefined threshold.

In an embodiment, the training dataset include (a) one or more atomic configurations of a chemical system with data for each configuration including cartesian coordinates of one or more atoms, (b) forces acting on the one or more atoms, and (c) a potential energy for each of the one or more atomic configurations. In an embodiment, the one or more shortlisted ACSFs corresponds to (a) a first shortlisted ACSF, (b) a second shortlisted ACSF, (c) a third shortlisted ACSF, and subsequent shortlisted ACSFs. In an embodiment, an ACSF from the sorted list of ACSFs with a highest spread is identified as the first shortlisted ACSF. In an embodiment, the second shortlisted ACSF is identified by traversing through the sorted list of ACSFs until an ACSF is identified whose pair-wise distance with the first shortlisted ACSF is greater than a predefined threshold. In an embodiment, the third shortlisted ACSF and the subsequent shortlisted ACSFs are identified as functions whose pair-wise distance with both the prior shortlisted ACSF is greater than the predefined threshold. In an embodiment, the step of traversing through the sorted list of ACSFs is reiteratively performed until there are no ACSFs whose pair-wise distance is greater than the predefined threshold with the prior shortlisted ACSFs. In an embodiment, a high dimensional neural network potential (HDNNP) is trained based on the optimal set of the one or more shortlisted ACSFs.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 3A-3D are exemplary flow diagrams illustrating method of determining the optimal set of the atom centered symmetry functions (ACSFs) to develop the accurate neural network potentials, according to some embodiments of the present disclosure.

DETAILED DESCRIPTION

Figure 1:
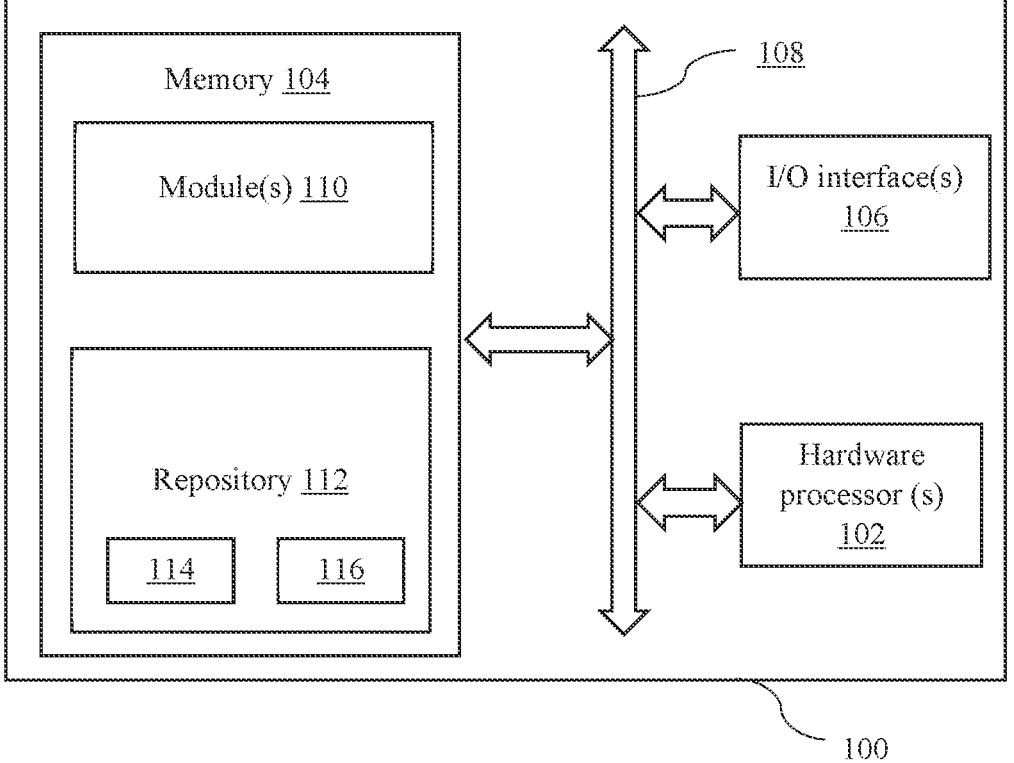
FIG. 1 illustrates a system to determine optimal set of atom centered symmetry functions (ACSFs) for developing accurate neural network potentials, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

There is a need for an approach to identify an optimal set of atom centered symmetry functions (ACSFs) which is crucial for the development of accurate neural network potentials i.e., high dimensional neural network potentials (HDNNP) for a chemical system. The chemical system is defined as a collection of interacting molecules. The ACSFs transform cartesian coordinates of atoms into a structural fingerprint that is invariant to rotation, translation, and atom index permutation. Embodiments of the present disclosure provide an automated framework to determine an optimal set of ACSFs to develop the HDNNP. The HDNNPs approximate a potential energy surface (PES) of the chemical system and can be used to perform molecular dynamics simulation to study time evolution of the system, identify equilibrium states at abinitio accuracies. The success of the HDNNP critically depends on use of an appropriate set of ACSFs.

Referring now to the drawings, and more particularly to FIGS. 1 through 5, where similar reference characters denote corresponding features consistently throughout the figures, there are shown preferred embodiments and these embodiments are described in the context of the following exemplary system and/or method.

FIG. 1 illustrates a system 100 to determine optimal set of atom centered symmetry functions (ACSFs) for developing accurate neural network potentials, according to some embodiments of the present disclosure. In an embodiment, the system 100 includes one or more processor(s) 102, communication interface device(s) or input/output (I/O) interface(s) 106, and one or more data storage devices or memory 104 operatively coupled to the one or more processor(s) 102. The memory 104 includes a database. The one or more processor(s) 102, the memory 104, and the I/O interface(s) 106 may be coupled by a system bus such as a system bus 108 or a similar mechanism. The one or more processor(s) 102 that are hardware processors can be implemented as one or more microprocessors, microcomputers, microcontrollers, digital signal processors, central processing units, state machines, logic circuitries, and/or any devices that manipulate signals based on operational instructions. Among other capabilities, the one or more processor(s) 102 is configured to fetch and execute computer-readable instructions stored in the memory 104. In an embodiment, the system 100 can be implemented in a variety of computing systems, such as laptop computers, notebooks, hand-held devices, workstations, mainframe computers, servers, a network cloud, and the like.

The I/O interface device(s) 106 can include a variety of software and hardware interfaces, for example, a web interface, a graphical user interface, and the like. The I/O interface device(s) 106 may include a variety of software and hardware interfaces, for example, interfaces for peripheral device(s), such as a keyboard, a mouse, an external memory, a camera device, and a printer. Further, the I/O interface device(s) 106 may enable the system 100 to communicate with other devices, such as web servers and external databases. The I/O interface device(s) 106 can facilitate multiple communications within a wide variety of networks and protocol types, including wired networks, for example, local area network (LAN), cable, etc., and wireless networks, such as Wireless LAN (WLAN), cellular, or satellite. In an embodiment, the I/O interface device(s) 106 can include one or more ports for connecting number of devices to one another or to another server.

The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 104 includes a module(s) 110 and a repository 112 for storing data processed, received, and generated by the module(s) 110. The module(s) 110 may include routines, programs, objects, components, data structures, and so on, which perform particular tasks, or implement particular abstract data types.

Further, a database in the repository 112 stores information pertaining to inputs fed to the system 100 and/or outputs generated by the system (e.g., data/output generated at each stage of the data processing) 100, specific to the methodology described herein. More specifically, the database stores information being processed at each step of the proposed methodology.

Additionally, the module(s) 110 may include programs or coded instructions that supplement applications and functions of the system 100. The repository 112, amongst other things, includes a system database 114 and other data 116. The other data 116 may include data generated as a result of the execution of one or more modules in the module(s) 110. Further, the database stores information pertaining to inputs fed to the system 100 and/or outputs generated by the system (e.g., at each stage), specific to the methodology described herein. Herein, the memory for example the memory 104 and the computer program code configured to, with the hardware processor for example the processor 102, causes the system 100 to perform various functions described herein under.

Figure 2:
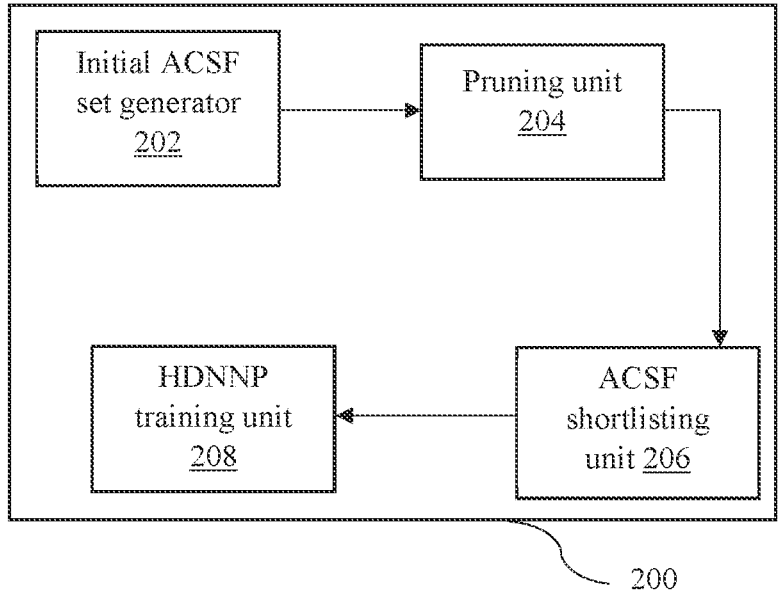
FIG. 2 illustrates an exemplary block diagram of the system of FIG. 1, according to some embodiments of the present disclosure.
Figure 3A:
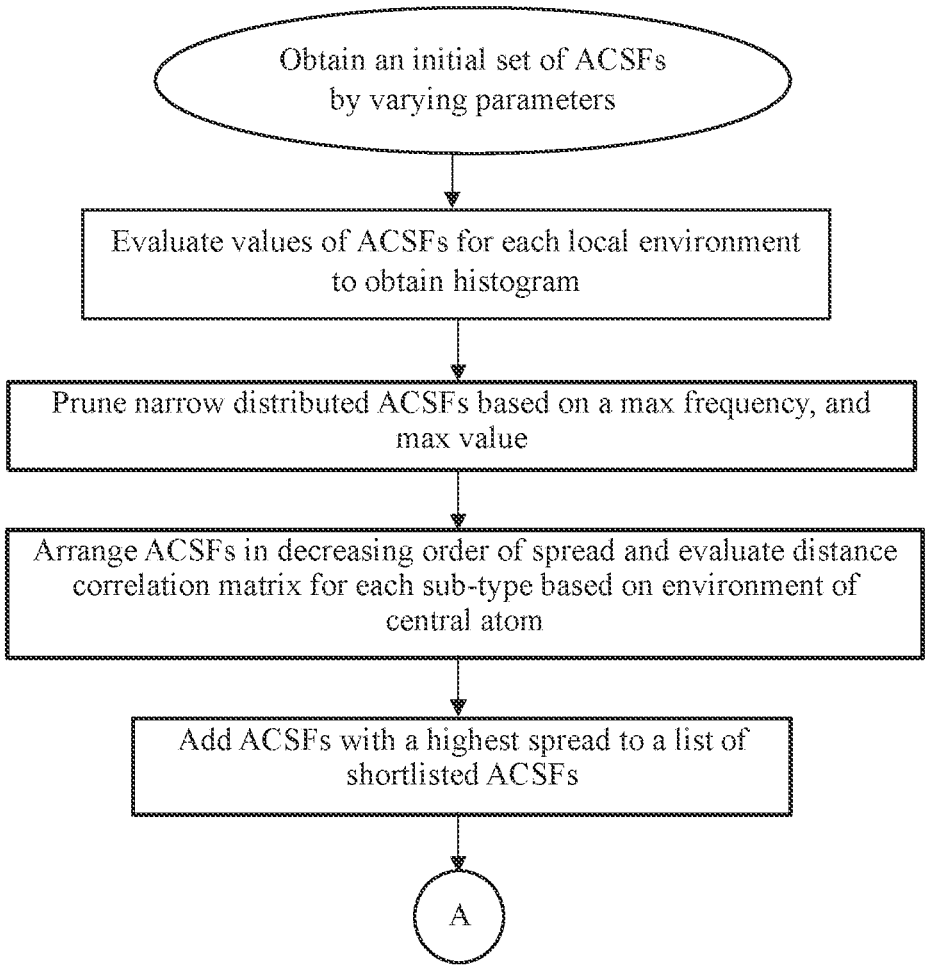
Figure 3B:
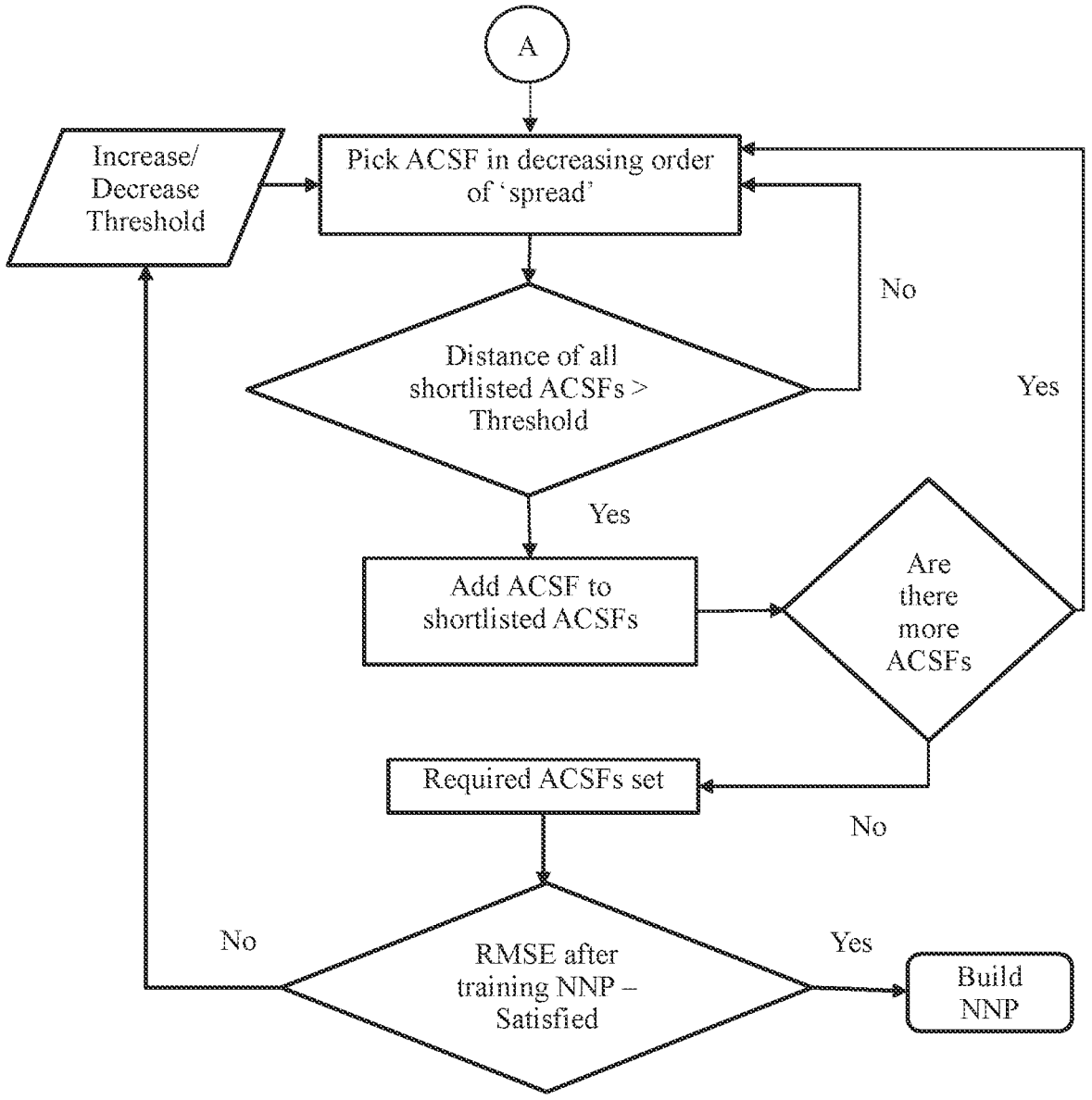
Figure 3C:
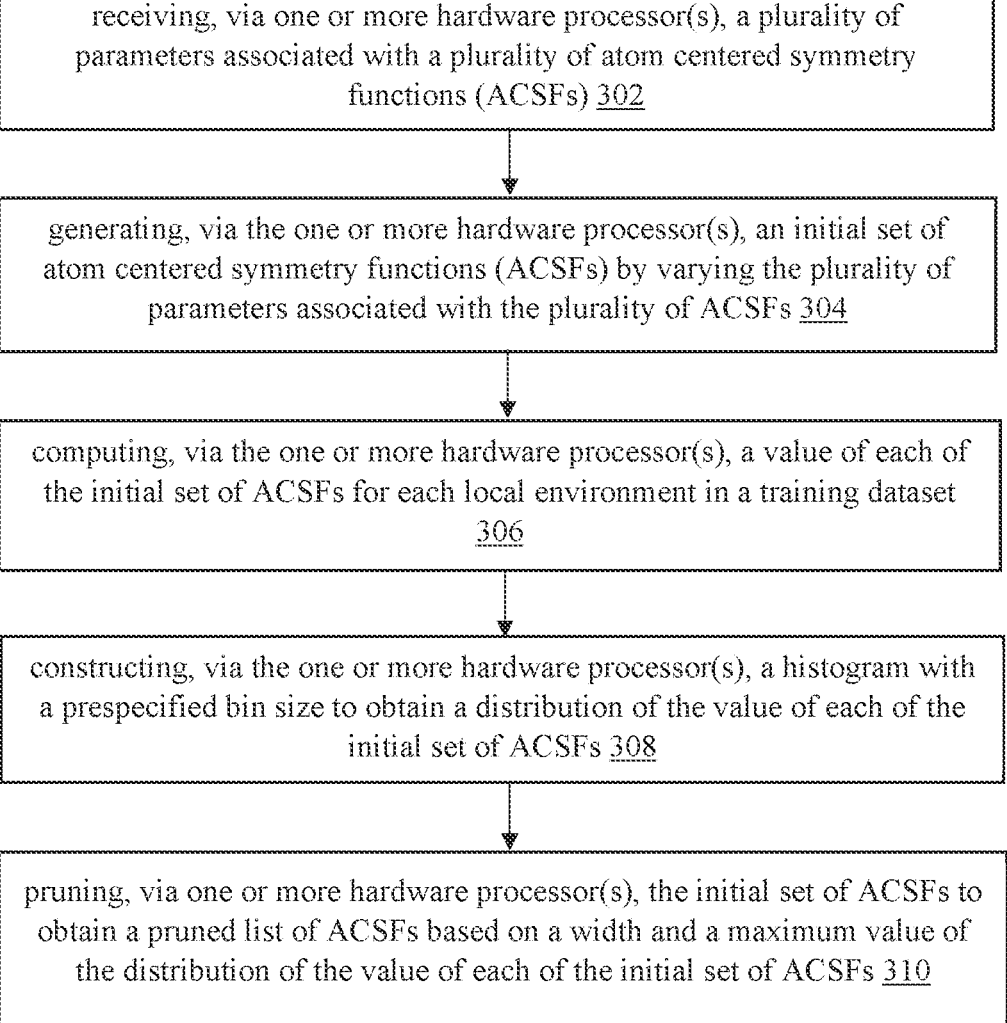

FIG. 2 illustrates an exemplary block diagram of the system 100 of FIG. 1, according to some embodiments of the present disclosure. The system 200 may be an example of the system 100 (FIG. 1). In an example embodiment, the system 200 may be embodied in, or is in direct communication with the system, for example the system 100 (FIG. 1). The system 200 is configured to identify an optimal set of ACSF for a given chemical system. The system 200 includes an initial ACSF set generator 202, a pruning unit 204, an ACSF shortlisting unit 206, and a HDNNP training unit 208. The initial ACSF set generator 202 is configured to obtain an initial set of ACSFs by varying the parameters associated with the ACSFs. The value of each of the generated initial set of ACSFs is computed for every micro-environment (e.g., region within a cut-off radius ($R_c$) from a central atom) present in an entire training dataset. The training dataset include cartesian coordinates of atoms in the chemical system for one or more configurations, forces acting on each atom, and total potential energy for each of the one or more atomic configurations. The ACSFs transform the Cartesian coordinates of each of the atoms in the chemical system into a corresponding structural fingerprint which is invariant to translation, rotation, and atom index permutation. A histogram with a predefined bin-size for the distribution of each of the ACSF values is constructed by evaluating the functional values of the ACSF for every micro-environment present in the training dataset. Based on the histograms, ACSF having a very narrow, delta function like distribution of values and those having a large 'maximum value' are eliminated in the initial pruning process. Interactions among various atoms of the chemical system define the energy. The interactions of a given atom with other atoms of the system within a predefined cutoff radius (e.g., 6 Å) is used. The local environment around an atom defines associated contribution towards the energy of the system.

The local environment around the atom is represented in form of two-body and three-body interactions using radial and angular type of ACSFs (highlighted in equations 1 and 2). Multiple ACSFs per element are used to transform the local environment of a given atom into corresponding 'structural fingerprint' such that a structure-energy relationship is learned by the neural network. With reference to below mentioned equations (1), (2), and (3), which depicts an example of typical radial and angular type ACSFs.

$$G_1^i = \sum_{j=1}^{N_{atom}} e^{-\eta(R_{ij}-R_s)^2} \cdot f_c(R_{ij}) \tag{1}$$

$$G_2^i = \tag{2}$$

$$2^{1-\zeta} \sum_{j\neq 1}^{N_{atom}} \sum_{k\neq i,j}^{N_{atom}} (1 + \lambda \cos\theta_{ijk})^\zeta e^{-\eta(R_{ij}-R_s)^2} \cdot f_c(R_{ij}) \cdot f_c(R_{jk}) \cdot f_c(R_{ik})$$

$$f_c(R_{ij}) = \left\{ \tanh^3\left[1 - \frac{R_{ij}}{R_c}\right] \right\}, \text{ for } R_{ij} \leq R_c \tag{3}$$

$$0, \text{ for } R_{ij} \geq R_c$$

Where, "i" represents the central atom, $R_{ij}$ is the distance between the central atom "i" and the surrounding atom "j", and $\theta_{ijk}$ is the angle subtended by the surrounding atoms 'j' and 'k' at the central atom 'i'.

The one or more parameters in equation 1. $\eta$, $R_s$ and $R_c$, and equation 2: $\zeta$, $\lambda$, $\eta$, $R_s$ and $R_c$ control the shapes of the radial ACSF and the angular ACSF, respectively. In addition, the values of transformed coordinates (i.e., structural fingerprint/input to the neural network) is defined for a given local environment of an atom. The automated framework is configured to generate the initial set of ACSF parameters. The parameters are varied over a finite range of values for the ACSF (e.g., radial+angular type). The functional values of each of the ACSFs are obtained for every micro-environment present in the dataset. The dataset is used to construct a histogram for every ACSF, to obtain a distribution of values assumed by the ACSF. Subsequently, ACSFs that have a very narrow 'delta-like' distribution of values and with a 'large' maximum value are eliminated from the dataset. A 'delta-like' distribution of an ACSF's value indicates that functional value of the ACSF is approximately same irrespective of the micro-environment of an atom and these functions are unable to distinguish between different micro-environments. The ACSF whose maximum value is 'large' may pose challenges while training the weights of the HDNNP. After eliminating such ACSFs, the remaining ACSFs are sorted in a decreasing order of the spread of their distributions.

$$spread = \left( \frac{normalized\ mean + normalized\ standard\ deviation}{1 + r_s} \right) \quad (4)$$

$r_s$—Distance from central atom where contribution of ACSF value is maximum.

To eliminate one or more redundant ACSFs, distance correlation is evaluated between every pair of the ACSF in the sorted list. For example, Wasserstein Distance (WD) between two distributions is used as a criteria to distinguish between any two ACSF, pairwise WD is evaluated for all the ACSF in the sorted list, which is used to shortlist final set of ACSFs. The ACSF with the largest 'spread' in the sorted list is considered as a first shortlisted ACSF. A second shortlisted ACSF is obtained by traversing through the sorted list of ACSFs until identifying a function whose WD with the first shortlisted ACSF is larger than a predefined threshold. This ACSF is then added to the one or more shortlisted ACSFs. A third shortlisted ACSF is then identified as that function whose WD with both the prior shortlisted functions is larger than the threshold. The previous step is repeated until no ACSFs is left whose WD is greater than the threshold with all the shortlisted functions. The procedure identifies a subset of ACSFs in which no two functions have a WD less than the threshold, thereby eliminating redundant ACSFs from the pruned subset. The number of ACSFs shortlisted by this procedure can be tweaked by changing the threshold, with a lower threshold resulting in a larger number of shortlisted ACSFs.

The optimal set of the one or more shortlisted ACSFs are used to train the HDNNP against energies and atomic forces of various configurations present in the training set. If the error incurred at the end of the training is larger than expected values (e.g., a larger than the errors in reference DFT calculations), the distance threshold is reduced to get a greater number of shortlisted ACSFs than the previous cases and the training process is repeated. On the contrary, if the error incurred at the end of training is much lower than the expectation and a small compromise on the accuracy is acceptable in favor of lower computational complexity, then the distance threshold can be increased to obtain a smaller set of ACSFs with which the HDNNP can be trained. An optimal set of the one or more shortlisted ACSFs can thus be obtained to build an accurate HDNNP.

FIGS. 3A-3D are exemplary flow diagrams 300 illustrating method of determining the optimal set of the atom centered symmetry functions (ACSFs) to develop the accurate neural network potentials, according to some embodiments of the present disclosure. In an embodiment, the system 100 comprises one or more data storage devices or the memory 104 operatively coupled to the one or more hardware processor(s) 102 and is configured to store instructions for execution of steps of the method by the one or more processor(s) 102. The flow diagram depicted is better understood by way of following explanation/description. The steps of the method of the present disclosure will now be explained with reference to the components of the system as depicted in FIGS. 1 and 2.

At step 302, one or more parameters associated with one or more atom centered symmetry functions (ACSFs) are received. At step 304, an initial set of atom centered symmetry functions (ACSFs) is generated by varying the one or more parameters associated with the one or more ACSFs. At step 306, a value of each of the initial set of atom centered symmetry functions (ACSFs) is computed for each local environment in a training dataset. Each local environment corresponds to a region within a cut-off radius ($R_c$) from a central atom. In an embodiment, the training dataset includes (a) one or more atomic configurations of a chemical system with data for each configuration which further include cartesian coordinates of one or more atoms, (b) forces acting on the one or more atoms, and (c) a potential energy for each of the one or more atomic configurations. At step 308, a histogram with a prespecified bin size is constructed to obtain a distribution of the value of each of the initial set of atom centered symmetry functions (ACSFs). At step 310, the initial set of ACSFs is pruned to obtain a pruned list of ACSFs based on a width and a maximum value of the distribution of the value of each of the initial set of atom centered symmetry functions (ACSFs). At step 312, the pruned list of ACSFs is sorted in a decreasing order of a spread to obtain a sorted list of atom centered symmetry functions (ACSFs).

At step 314, an optimal set of one or more shortlisted ACSFs is determined by traversing through the sorted list of ACSFs. A pair-wise distance between a distribution of each of the one or more shortlisted ACSFs is greater than a predefined threshold. In an embodiment, the one or more shortlisted ACSFs corresponds to (a) a first shortlisted ACSF, (b) a second shortlisted ACSF, (c) a third shortlisted ACSF, and subsequent shortlisted ACSFs. In an embodiment, an ACSF from the sorted list of ACSFs with a highest spread is identified as the first shortlisted ACSF. In an embodiment, the second shortlisted ACSF is identified by traversing through the sorted list of ACSFs until an ACSF is identified whose pair-wise distance with the first shortlisted ACSF is greater than a predefined threshold. In an embodiment, the third shortlisted ACSF and the subsequent shortlisted ACSFs are identified as functions whose pair-wise distance with both the prior shortlisted ACSFs is greater than the predefined threshold.

At step 316, the step of traversing through the sorted list of ACSFs is reiteratively performed until there are no ACSFs whose pair-wise distance is greater than the predefined threshold with the prior shortlisted ACSFs. At step 318, a high dimensional neural network potential (HDNNP) is trained based on the optimal set of the one or more shortlisted ACSFs.

EXPERIMENTAL RESULTS

For example, a HDNNP was developed for bulk water system. The proposed framework was used to identify an optimal set of ACSFs and generate an HDNNP for bulk water, by training on the RPBE-D3 dataset which is publicly available so that the developed HDNNP can be used to study the dynamics of water at abinitio accuracies, but at a much lower computational cost. Water includes two atom types, namely Hydrogen (H) and Oxygen (O). Considering the central atom 'i' as O, there are two sub-types of radial ACSF, where surrounding atom 'j' is O in one case and H in the other case. There are three types of angular ACSFs where (j, k) atoms being (H, H), (H, O) and (O, O). Similarly, the radial ACSFs of H are H—H, H—O, where atom before hyphen represents the central atom and atom after hyphen represents the surrounding atom. The angular ACSFs of H are represented as H—H H, H—H O, H—O O. All ACSFs with central atom as H and O act as input to neural network of atoms H and O respectively. A diverse set of ACSFs of each sub-type of radial and angular ACSFs of H and O is needed to fit an accurate HDNNP. The method to get O—O type of ACSF for bulk water system is described. An initial huge set of relevant ACSFs were chosen for which the values for $\eta$, $r_s$, $\zeta$ and $\lambda$ were chosen in the range of (0.001, 2.1), (0, 10), (−1, 4) and (−1, 1) respectively, giving a total of 10,400 ACSFs. Specifically, for the O—O ACSFs, these parameter values resulted in 1400 functions. Functional values of these 1400 ACSFs is evaluated for all the microenvironments in the training dataset and histograms were constructed with a bin size of 1E−03. ACSFs with a narrow delta-like distribution of values, defined by maximum frequency being larger than 5000, were eliminated. In addition, ACSFs with a maximum function value larger than 10 were also eliminated. This resulted in 454 O—O ACSFs after first pruning. These 454 ACSFs are arranged in decreasing order of spread {(normalized mean+normalized standard deviation)/(1+$r_s$)}. Wasserstein Distance between the distribution of every pair of pruned ACSF was calculated. Then, a threshold of 0.185 times the maximum Wasserstein Distance was used to shortlist the final set of ACSFs. This resulted in 8 ACSFs of O—O sub-type. Similarly, the process of shortlisting was carried out on all the sub-types of ACSFs.

Table 1 shows the number of ACSFs of all subtypes at different stages.

TABLE 1

| Central Atom | ACSF Type | Sub-type | Initial Set | First Pruning | Final Number of SFs | Total |
|---|---|---|---|---|---|---|
| H | Radial | H—H | 1400 | 280 | 8 | |
| | Radial | H—O | 1400 | 611 | 12 | |
| | Angular | H—H H | 800 | 28 | 4 | 35 |
| | Angular | H—H O | 800 | 60 | 6 | |
| | Angular | H—O O | 800 | 50 | 5 | |
| O | Radial | O—H | 1400 | 386 | 10 | |
| | Radial | O—O | 1400 | 454 | 8 | |
| | Angular | O—H H | 800 | 90 | 6 | 34 |
| | Angular | O—H O | 800 | 56 | 6 | |
| | Angular | O—O O | 800 | 17 | 4 | |
| | Total | | 10400 | 2032 | 69 | |

The training data for parametrizing the NNP contained configurations from liquid water and various forms of ice. Table 2 reports the accuracies of the NNPs constructed using the shortlisted set of ACSFs. ACSF identified by the methodology resulted in a slightly better fit to the dataset albeit using a similar number of functions as earlier works.

TABLE 2

| | RMSE Energies (meV/atom) | RMSE Forces (meV/Å) |
|---|---|---|
| Resultant ACSF | 0.778 | 40.3 |
| ACSF in existing art | 1.17 | 43.7 |

Figure 4A:
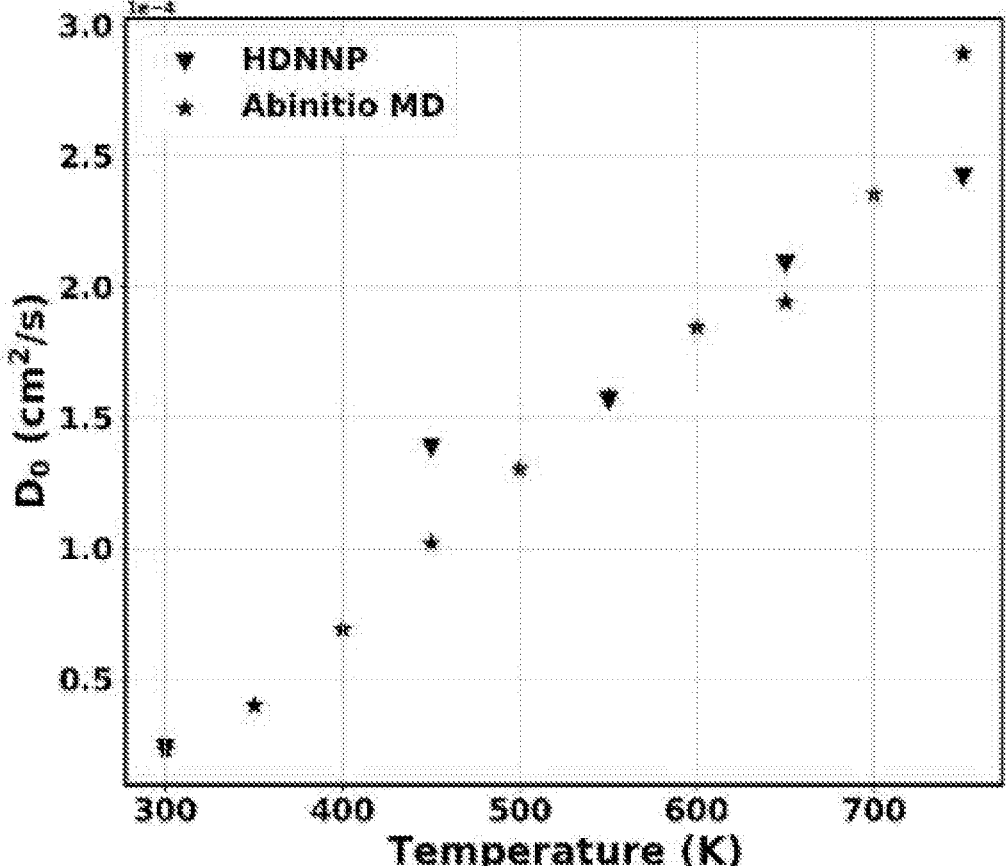
FIG. 4A and FIG. 4B are exemplary graphical representations of diffusivity of water computed using a newly developed HDNNP and an ab-initio MD, according to some embodiments of the present disclosure.
Figure 4B:
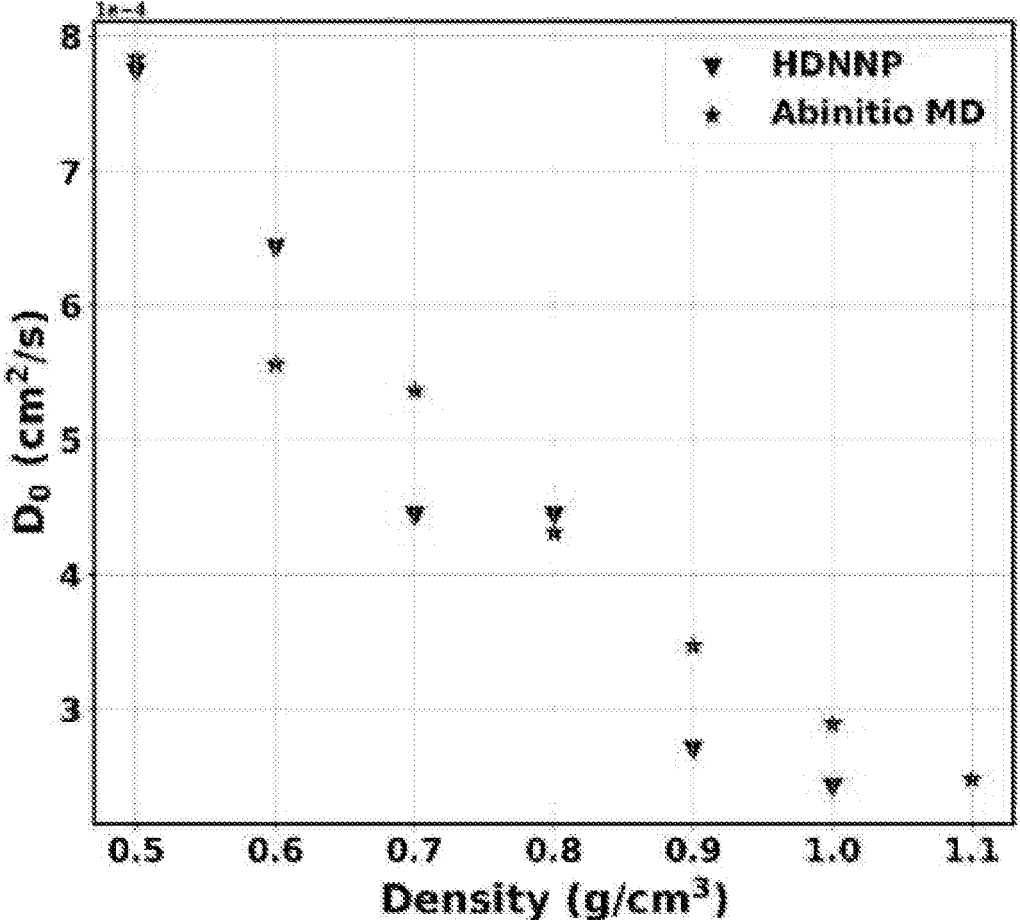
Figure 5:
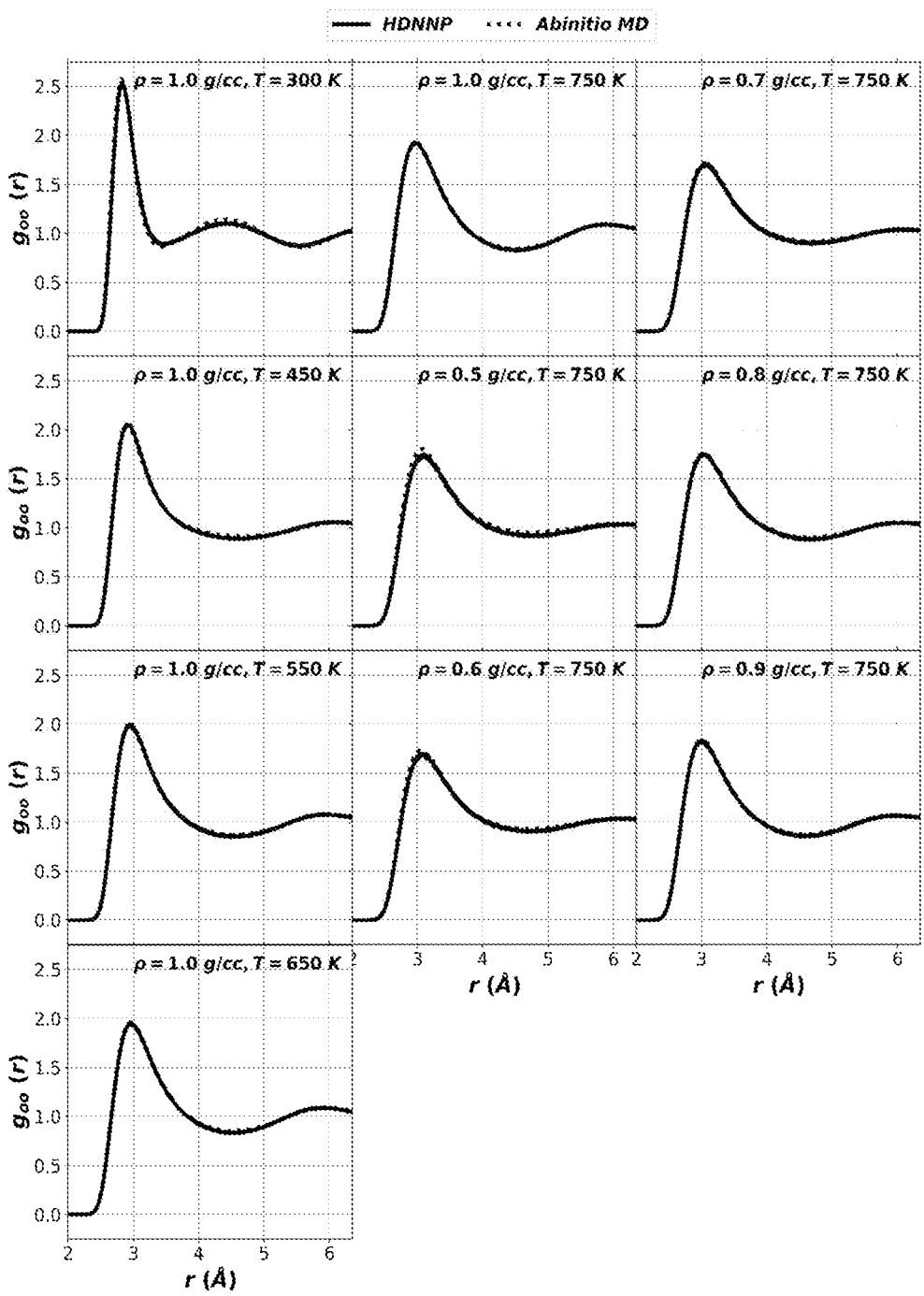
FIG. 5 is an exemplary graphical representation of O—O RDF computed with the newly developed HDNNP and the ab-initio MD, according to some embodiments of the present disclosure.

With reference to FIG. 4A and FIG. 4B are exemplary graphical representations of diffusivity of water computed using a newly developed HDNNP and an ab-initio MD, according to some embodiments of the present disclosure. FIG. 5 is an exemplary graphical representation of O—O RDF computed with the newly developed HDNNP and the ab-initio MD, according to some embodiments of the present disclosure. The newly developed HDNNP was used to perform MD simulations of bulk water at 750K, 650K, 550K, 450K, 300K at 1 g/cc density. In addition, simulations were also carried out for 0.5, 0.6, 0.7, 0.8, 0.9 g/cc densities at a temperature of 750K. All these simulations were carried out with a system containing 512 water molecules. Clearly, the HDNNP developed with the optimal set of ACSFs can closely match the ab-initio values, attesting to an accuracy.

The embodiment of present disclosure herein addresses unresolved problem of the currently used trial-and-error strategy for the identification of an optimal set of ACSFs to develop accurate HDNNP for any chemical system. The embodiment of present disclosure herein provides a systematic framework to determine the optimal set of the atom centered symmetry functions (ACSFs) for developing the neural network potentials i.e., accurate HDNNP for a chemical system. The embodiment of present disclosure herein considers an inherent variability in micro-environments present in a training dataset as well as account for an inter-ACSF correlations to identify the optimal set of ACSFs. The claimed approach is generic in nature and applicable to both reactive and non-reactive systems.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:
1. A processor-implemented method, comprising:
receiving, via one or more hardware processor(s), a plurality of parameters associated with a plurality of atom centered symmetry functions (ACSFs);

12 generating, via the one or more hardware processor(s), an initial set of atom centered symmetry functions (ACSFs) by varying the plurality of parameters associated with the plurality of ACSFs;

computing, via the one or more hardware processor(s), a value of each of the initial set of ACSFs for each local environment in a training dataset, wherein each local environment corresponds to a region within a cut-off radius ($R_c$) from a central atom;

constructing, via the one or more hardware processor(s), a histogram with a prespecified bin size to obtain a distribution of the value of each of the initial set of ACSFs;

pruning, via the one or more hardware processor(s), the initial set of ACSFs to obtain a pruned list of ACSFs based on a width and a maximum value of the distribution of the value of each of the initial set of ACSFs;

sorting, via the one or more hardware processor(s), the pruned list of ACSFs in a decreasing order of a spread to obtain a sorted list of atom centered symmetry functions (ACSFs); and determining, via the one or more hardware processor(s), an optimal set of a plurality of shortlisted ACSFs by traversing through the sorted list of ACSFs, and wherein a pair-wise distance between a distribution of each of the plurality of shortlisted ACSFs is greater than a predefined threshold.

2. The processor implemented method of claim 1, wherein the training dataset comprises of (a) a plurality of atomic configurations of a chemical system with data for each configuration comprising cartesian coordinates of a plurality of atoms, (b) forces acting on the plurality of atoms, and (c) a potential energy for each of the plurality of atomic configurations.

3. The processor implemented method of claim 1, wherein the plurality of shortlisted ACSFs corresponds to (a) a first shortlisted ACSF, (b) a second shortlisted ACSF, (c) a third shortlisted ACSF, and subsequent shortlisted ACSFs, wherein an ACSF from the sorted list of ACSFs with a highest spread is identified as the first shortlisted ACSF, wherein the second shortlisted ACSF is identified by traversing through the sorted list of ACSFs until an ACSF is identified whose pair-wise distance with the first shortlisted ACSF is greater than a predefined threshold, and wherein the third shortlisted ACSF and the subsequent shortlisted ACSFs are identified as functions whose pair-wise distance with both the prior shortlisted ACSFs is greater than the predefined threshold.

4. The processor implemented method of claim 3, further comprising, reiteratively performing, via the one or more hardware processor(s), the step of traversing through the sorted list of ACSFs until there are no ACSFs whose pair-wise distance is greater than the predefined threshold with the prior shortlisted ACSFs.

5. The processor implemented method of claim 1, further comprising, training, via the one or more hardware processor(s), a high dimensional neural network potential (HDNNP) based on the optimal set of the plurality of shortlisted ACSFs.

6. A system, comprising:
a memory storing instructions;
one or more communication interfaces; and
one or more hardware processor(s) coupled to the memory via the one or more communication interfaces, wherein the one or more hardware processor(s) are configured by the instructions to:
receive, a plurality of parameters associated with a plurality of atom centered symmetry functions (ACSFs);

generate, an initial set of atom centered symmetry functions (ACSFs) by varying the plurality of parameters associated with the plurality of ACSFs;

compute, a value of each of the initial set of ACSFs for each local environment in a training dataset, wherein each local environment corresponds to a region within a cut-off radius (Rc) from a central atom;

construct, a histogram with a prespecified bin size to obtain a distribution of the value of each of the initial set of ACSFs;

prune, the initial set of ACSFs to obtain a pruned list of ACSFs based on a width and a maximum value of the distribution of the value of each of the initial set of ACSFs;

sort, the pruned list of ACSFs in a decreasing order of a spread to obtain a sorted list of atom centered symmetry functions (ACSFs); and determine, an optimal set of a plurality of shortlisted ACSFs by traversing through the sorted list of ACSFs, and wherein a pair-wise distance between a distribution of each of the plurality of shortlisted ACSFs is greater than a predefined threshold.

7. The system of claim 6, wherein the training dataset comprises of (a) a plurality of atomic configurations of a chemical system with data for each configuration comprising cartesian coordinates of a plurality of atoms, (b) forces acting on the plurality of atoms, and (c) a potential energy for each of the plurality of atomic configurations.

8. The system of claim 6, wherein the plurality of shortlisted ACSFs corresponds to (a) a first shortlisted ACSF, (b) a second shortlisted ACSF, (c) a third shortlisted ACSF, and subsequent shortlisted ACSFs, wherein an ACSF from the sorted list of ACSFs with a highest spread is identified as the first shortlisted ACSF, wherein the second shortlisted ACSF is identified by traversing through the sorted list of ACSFs until an ACSF is identified whose pair-wise distance with the first shortlisted ACSF is greater than a predefined threshold, and wherein the third shortlisted ACSF and the subsequent shortlisted ACSFs are identified as functions whose pair-wise distance with both the prior shortlisted ACSFs is greater than the predefined threshold.

9. The system of claim 8, wherein the one or more hardware processor(s) are further configured by the instructions to reiteratively perform the step of traversing through the sorted list of ACSFs until there are no ACSFs whose pair-wise distance is greater than the predefined threshold with the prior shortlisted ACSFs.

10. The system of claim 6, wherein the one or more hardware processor(s) are further configured by the instructions to train, a high dimensional neural network potential (HDNNP) based on the optimal set of the plurality of shortlisted ACSFs.

11. One or more non-transitory machine-readable information storage mediums comprising one or more instructions which when executed by one or more hardware processors cause:

receiving, a plurality of parameters associated with a plurality of atom centered symmetry functions (ACSFs);

generating, an initial set of atom centered symmetry functions (ACSFs) by varying the plurality of parameters associated with the plurality of ACSFs;

computing, a value of each of the initial set of ACSFs for each local environment in a training dataset, wherein each local environment corresponds to a region within a cut-off radius ($R_c$) from a central atom;

constructing, a histogram with a prespecified bin size to obtain a distribution of the value of each of the initial set of ACSFs;

pruning, the initial set of ACSFs to obtain a pruned list of ACSFs based on a width and a maximum value of the distribution of the value of each of the initial set of ACSFs;

sorting, the pruned list of ACSFs in a decreasing order of a spread to obtain a sorted list of atom centered symmetry functions (ACSFs); and determining, an optimal set of a plurality of shortlisted ACSFs by traversing through the sorted list of ACSFs, and wherein a pair-wise distance between a distribution of each of the plurality of shortlisted ACSFs is greater than a predefined threshold.

12. The one or more non-transitory machine-readable information storage mediums of claim 11, wherein the training dataset comprises of (a) a plurality of atomic configurations of a chemical system with data for each configuration comprising cartesian coordinates of a plurality of atoms, (b) forces acting on the plurality of atoms, and (c) a potential energy for each of the plurality of atomic configurations.

13. The one or more non-transitory machine-readable information storage mediums of claim 11, wherein the plurality of shortlisted ACSFs corresponds to (a) a first shortlisted ACSF, (b) a second shortlisted ACSF, (c) a third shortlisted ACSF, and subsequent shortlisted ACSFs, wherein an ACSF from the sorted list of ACSFs with a highest spread is identified as the first shortlisted ACSF, wherein the second shortlisted ACSF is identified by traversing through the sorted list of ACSFs until an ACSF is identified whose pair-wise distance with the first shortlisted ACSF is greater than a predefined threshold, and wherein the third shortlisted ACSF and the subsequent shortlisted ACSFs are identified as functions whose pair-wise distance with both the prior shortlisted ACSFs is greater than the predefined threshold.

14. The one or more non-transitory machine-readable information storage mediums of claim 13, reiteratively performing, the step of traversing through the sorted list of ACSFs until there are no ACSFs whose pair-wise distance is greater than the predefined threshold with the prior shortlisted ACSFs.

15. The one or more non-transitory machine-readable information storage mediums of claim 11, training, a high dimensional neural network potential (HDNNP) based on the optimal set of the plurality of shortlisted ACSFs.

* * * * *